United States Patent
Wu et al.

(10) Patent No.: US 9,778,163 B2
(45) Date of Patent: *Oct. 3, 2017

(54) NUCLEATED RED BLOOD CELL ANALYSIS SYSTEM AND METHOD

(71) Applicant: Abbott Laboratories, Abbott Park, IL (US)

(72) Inventors: Jiong Wu, Los Gatos, CA (US); Marilou Coleman, Newark, CA (US); Emily H. Lin, Cupertino, CA (US); Michael R. Buhl, San Ramon, CA (US); Giacomo Vacca, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 157 days.

This patent is subject to a terminal disclaimer.

(21) Appl. No.: 14/808,720

(22) Filed: Jul. 24, 2015

(65) Prior Publication Data

US 2016/0018312 A1   Jan. 21, 2016

Related U.S. Application Data

(63) Continuation of application No. 13/456,738, filed on Apr. 26, 2012, now Pat. No. 9,103,759.

(60) Provisional application No. 61/482,545, filed on May 4, 2011.

(51) Int. Cl.
| | |
|---|---|
| *G01N 15/14* | (2006.01) |
| *G01N 33/49* | (2006.01) |
| *G01N 21/64* | (2006.01) |
| *G01N 33/80* | (2006.01) |
| *G01N 15/00* | (2006.01) |
| *G01N 15/10* | (2006.01) |

(52) U.S. Cl.
CPC ....... *G01N 15/1434* (2013.01); *G01N 15/147* (2013.01); *G01N 15/1459* (2013.01); *G01N 21/6428* (2013.01); *G01N 33/49* (2013.01); *G01N 33/80* (2013.01); *G01N 2015/008* (2013.01); *G01N 2015/0069* (2013.01); *G01N 2015/1006* (2013.01); *G01N 2015/1402* (2013.01); *G01N 2015/1477* (2013.01); *G01N 2015/1488* (2013.01); *G01N 2021/6439* (2013.01)

(58) Field of Classification Search
None
See application file for complete search history.

(56) References Cited

U.S. PATENT DOCUMENTS

| | | |
|---|---|---|
| 4,661,913 A | 4/1987 | Wu et al. |
| 4,727,020 A | 2/1988 | Recktenwald |
| 4,882,284 A | 11/1989 | Kirchanski et al. |
| 5,559,037 A | 9/1996 | Kim et al. |
| 5,631,165 A | 5/1997 | Chupp et al. |
| 5,656,499 A | 8/1997 | Chupp et al. |
| 5,776,709 A | 7/1998 | Jackson et al. |
| 5,812,419 A | 9/1998 | Chupp et al. |
| 5,879,900 A | 3/1999 | Kim et al. |
| 5,891,734 A | 4/1999 | Gill et al. |
| 5,928,949 A | 7/1999 | Sakata et al. |
| 5,939,326 A | 8/1999 | Chupp et al. |
| 6,197,593 B1 | 3/2001 | Deka et al. |
| 6,228,652 B1 | 5/2001 | Rodriguez et al. |
| 6,551,831 B2 | 4/2003 | Gupta et al. |
| 7,299,135 B2 | 11/2007 | Thayer |
| 7,638,290 B2 | 12/2009 | Lefevre et al. |
| 2004/0265830 A1 | 12/2004 | Szabo et al. |
| 2006/0269970 A1 | 11/2006 | Paul et al. |
| 2007/0111276 A1 | 5/2007 | Lefevre et al. |
| 2007/0287145 A1 | 12/2007 | Mizukami et al. |
| 2007/0298408 A1 | 12/2007 | Mizukami et al. |
| 2009/0023129 A1 | 1/2009 | Xu et al. |
| 2009/0061478 A1 | 3/2009 | Poulsen et al. |

(Continued)

FOREIGN PATENT DOCUMENTS

| | | |
|---|---|---|
| JP | H0599919 | 4/1993 |
| JP | H06501106 | 1/1994 |
| JP | H09508703 | 9/1997 |

(Continued)

OTHER PUBLICATIONS

BD LSR II Flow Cytometer Brochure, BD Biosciences (2003).
Champert et al. (2004) "White-light supercontinuum generation in normally dispersive optical fiber using original multi-wavelength pumping system" Optics Express 12(19):4366-4371.
De Grooth et al. (1987) "Light-Scattering Polarization Measurements as a New Parameter in Flow Cytometry" *Cytometry* 8:539-544.
Flowguide, Flow cytometry guide, abcam® (2013).
Flowguide, Introduction to Flow Cytometry: A Learning Guide, Technical Manual, BD Biosciences (Apr. 2000).

(Continued)

*Primary Examiner* — Taeyoon Kim
*Assistant Examiner* — Srikanth Patury
(74) *Attorney, Agent, or Firm* — Edward J. Baba; Bozicevic, Field & Francis LLP (57) ABSTRACT

Systems and methods for analyzing blood samples, and more specifically for performing a nucleated red blood cell (nRBC) analysis. The systems and methods screen a blood sample by means of fluorescence staining and a fluorescence triggering strategy, to identify nuclei-containing particles within the blood sample. As such, interference from unlysed red blood cells (RBCs) and fragments of lysed RBCs is substantially eliminated. The systems and methods also enable development of relatively milder reagent(s), suitable for assays of samples containing fragile white blood cells (WBCs). In one embodiment, the systems and methods include: (a) staining a blood sample with an exclusive cell membrane permeable fluorescent dye; (b) using a fluorescence trigger to screen the blood sample for nuclei-containing particles; and (c) using measurements of light scatter and fluorescence emission to distinguish nRBCs from WBCs.

17 Claims, 11 Drawing Sheets

(56) References Cited

U.S. PATENT DOCUMENTS

2010/0273168 A1  10/2010  Krockenberger et al.

FOREIGN PATENT DOCUMENTS

| JP | H09508705 | 9/1997 |
| JP | 2938976 | 6/1999 |
| JP | 2000501838 | 2/2000 |
| JP | 2001091513 | 4/2001 |
| JP | 2003510557 | 3/2003 |
| JP | 2003310299 | 11/2003 |
| JP | 2008500558 | 1/2008 |
| JP | 2010513929 | 4/2010 |
| JP | 2011069707 | 4/2011 |
| JP | 2013592594 | 1/2013 |
| WO | 2009001868 | 12/2008 |
| WO | 2010011583 | 1/2010 |
| WO | 2011028437 | 3/2011 |

OTHER PUBLICATIONS

Fluorochromes, Table of Fluorochromes, SALK CCMI (2008).
LTAC Preservatives Handbook, 2013.
McCoy et al. (1991) "Sorting Minor Subpopulations of Cells: Use of Fluorescence as the Triggering Signal" *Cytometry* 12:268-274.
Sakata (2000) "Reagent Characteristics in the XE-2100 NRBC Channel" Sysmex Journal International, Technical Report, Series 9, 10(1):41-46.
Sysmex "Action mechanism of leukocytes by special reagents for automated leukocyte differentiation (DIFF channel)" The Cell Analysis Center—Scientific Bulletin Part 5, 2008, XP055183570.
Sysmex XE-2100 Operator's Manual, Chapter 7, Functional Description, Revised Jul. 2007, XP55182265.
SYTO-Dyes, Invitrogen Nucleic Staining Dyes, Webpage, 2009.
SYTO-Dyes, Molecular Probes Handbook, Table 8.3, 2009.

NUCLEATED RED BLOOD CELL ANALYSIS SYSTEM AND METHOD

CROSS REFERENCE TO RELATED APPLICATIONS

This application claims the benefit under 35 U.S.C. §119(e) of U.S. Provisional Patent Application No. 61/482,545, titled, Method For Analyzing Nucleated Red Blood Cells, and filed on May 4, 2011, the entire disclosure of which is incorporated by reference herein.

This application is also related to application Ser. No. 13/456,729, filed on Apr. 26, 2012, titled "WHITE BLOOD CELL ANALYSIS SYSTEM AND METHOD," and application Ser. No. 13/456,744, filed on Apr. 26, 2012, titled "BASOPHIL ANALYSIS SYSTEM AND METHOD," the entire disclosures of which are herein incorporated by reference in their entirety.

BACKGROUND

This invention relates to hematology systems and methods. More specifically, this invention relates to systems and methods for analyzing blood samples to identify, classify, and/or quantify nucleated red blood cells (nRBCs) in a sample of blood.

Nucleated red blood cells are often present in the fetus and in the peripheral blood of newborns. However, nRBCs are considered to be abnormal for adults. The presence of nRBCs in an adult's peripheral blood stream is usually an indication of serious marrow stress. Studies have shown that the appearance of nRBCs in the blood stream is highly correlated with severe disease stages and/or poor prognosis for critically ill patients. Therefore, accurate identification and quantification of nRBCs has become increasingly important for clinical diagnostics.

Because nRBCs share numerous similarities with white blood cells (WBCs), the concentration of nRBCs in a blood sample is typically reported as a percentage of total WBCs in the blood sample (i.e., % nRBC=nRBCs/WBCs×100%). Traditional approaches to analyze nRBCs include: (1) separating nRBCs from WBCs by size; (2) differentiating nRBCs from WBCs by means of light scattering; or (3) analyzing nRBCs by means of fluorescence emission detection after lysis and staining with a cell membrane impermeable fluorescent dye(s).

Each of the above-listed techniques has shown weaknesses in clinical practices. For example, it is difficult to completely eliminate fragments of lysed red blood cells (RBCs) in rapid hematology measurements. Because fragments of RBCs and the nuclei of nRBCs may be similar in size and light scattering characteristics, analysis based on size and/or light scattering is sometimes misleading. Meanwhile, analysis based on fluorescence emission may be adversely affected by: (1) "under-lysing" of the sample such that the cell membrane impermeable dye cannot reach the nuclei of the nRBCs; (2) "over-lysing" of the sample such that nuclei of the WBCs are stained and interfere with the nRBC count; (3) the existence of fragile lymphocytes, such that WBCs are unexpectedly hyper-sensitive to a lysing reagent (giving false positives); and/or (4) the existence of lyse-resistant nRBCs, such that the nRBCs are unexpectedly insensitive to a lysing reagent (giving false negatives). In practice, over-lysing or under-lysing is common on account of the variation in membrane rigidity of blood cells among samples of blood. As such, dependence on known light scatter and/or fluorescence emission detection techniques may result in an inaccurate and unreliable analysis for nRBCs, thereby preventing correct diagnoses and treatment for critically ill patients.

BRIEF SUMMARY

Provided herein are systems and methods for analyzing blood samples, and more specifically for performing a nRBC analysis. The systems and methods screen a blood sample by means of fluorescence staining with a cell membrane permeable fluorescent dye. A fluorescence triggering strategy is then used to identify, distinguish, and separate nuclei-containing particles (e.g., nRBCs and WBC) from non-nuclei-containing particles (e.g., RBCs and/or RBC fragments) within the blood sample. As such, interference from unlysed RBCs and fragments of lysed RBCs can be substantially eliminated prior to subsequent analysis. For example, in one embodiment, the systems and methods include: (a) staining a blood sample with an exclusive cell membrane permeable fluorescent dye; (b) using a fluorescence trigger to screen the blood sample for nuclei-containing particles; and then (c) using measurements of light scatter and fluorescence emission to distinguish nRBCs from WBCs. The systems and methods enable development of relatively milder reagent(s), suitable for assays of samples containing fragile WBCs.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the systems and methods presented. In the drawings, like reference numbers indicate identical or functionally similar elements.

FIG. 1A is a histogram showing measurements of axial light loss (ALL).

FIG. 1B is a histogram showing measurements of intermediate angle scatter (IAS).

FIG. 1C is a histogram showing measurements of 90° polarized side scatter (PSS).

FIG. 1D is a histogram showing measurements of fluorescence (FL1).

FIGS. 3A-3F are cytograms illustrating an analysis of a sample of blood containing nRBCs at a % NRBC of 75%.

FIGS. 4A-4F are cytograms illustrating an analysis of a sample of blood containing nRBCs as a % NRBC of 1.0%.

DETAILED DESCRIPTION

Provided herein are systems and methods for analyzing blood samples, and more specifically for performing an nRBC analysis to identify, classify, and count nRBCs in a blood sample. In general, the systems and methods disclosed screen nuclei-containing events vs. non-nuclei-containing events by means of fluorescence staining and a fluorescence triggering strategy. As such, interference from unlysed red blood cells (RBCs), such as lysis-resistant red blood cells (rstRBCs), and RBC fragments is substantially eliminated prior to subsequent analysis. In other words, the systems and methods described herein utilize at least one fluorescent dye and a fluorescence triggering system to screen events containing nuclei, to thereby accurately and reliably identify and quantify WBCs and nRBCs. A combination light scattering information and fluorescence information is then used to further separate nRBCs from WBCs. The systems and methods disclosed thereby ensure accurate counting and differentiation of nRBCs, WBCs, and WBC sub-populations. The systems and methods also enable development of relatively milder WBC reagent(s), suitable for assays of samples containing fragile lymphocytes (or other fragile WBCs), including aged samples.

In one embodiment, for example, the systems and methods disclosed herein include: (a) staining a blood sample with an exclusive cell membrane permeable fluorescent dye; (b) using a fluorescence trigger to screen the blood sample for nuclei-containing particles; and (c) using measurements of light scatter and fluorescence emission to distinguish nRBCs from WBCs. Systems and methods in accordance with the present invention show great advantages over traditional methods because the interference from fragments of RBCs is substantially eliminated, and the results of the assay become much less sensitive to the lysing strength. In other words, traditional nRBC analysis techniques are highly sensitive to lysing strength. If the strength of the lysing agent is too weak, the fragments of RBCs or unlysed RBCs were also collected in the analysis of WBCs. These fragments of RBCs or unlysed RBCs overlapped nRBCs in many dimensions, resulting in difficulty in analyzing nRBCs. On the other hand, if the strength of the lysing agent was too strong (in order to better deal with fragments of RBCs), a certain percentage of lymphocytes could be damaged and could be recognized as nRBCs. Therefore, the strength of the lysing agent is a problem in the analysis of WBCs. A key feature of the methods described herein is the reduction of interference from RBC fragments or unlysed RBCs in the analysis of WBCs and nRBCs. Accordingly, variations in the strength of the lysing agent can be better tolerated. Even if the lysing agent is weaker than usual, the unlysed RBCs do not interfere with the assay for nRBCs.

In the systems and methods described herein, quantification and identification of nRBCs and WBCs can be obtained simultaneously in a single assay. Alternatively, in the systems and methods described herein, quantification and identification of nRBCs can be carried out without analysis of WBCs.

(1) Use of Fluorescent Dye(s).

WBCs and nRBCs contain a relatively high concentration of DNA in their nuclei. Mature RBCs, however, do not contain DNA. Therefore, a fluorescent dye is selected to differentiate two classes of blood cells; namely, the blood cells containing nucleic acids and the blood cells not containing nucleic acids. The purpose of the dye is to penetrate into live cells easily, bind DNA with high affinity, and emit strong fluorescence with adequate Stokes shift when the dye is excited by an appropriate source of light. The peak absorption of the dye in the visible band substantially matches the wavelength of the source of light (within 50 nm of the wavelength of the source of light, more preferably, within 25 nm of the wavelength of the source of light), in order to be properly excite the dye and achieve optimal results.

The fluorescent dye selected is preferably: 1) capable of binding nucleic acids, 2) capable of penetrating cell membranes of WBCs and nRBCs, 3) excitable at a selected wavelength when subjected to a source of light, 4) emits fluorescence upon excitation by the source of light, and 5) is biostable and soluble in a liquid. The dye may be selected from group consisting of: acridine orange, SYBR 11, SYBR Green series dye, hexidium iodide, SYTO 11, SYTO 12, SYTO 13, SYTO 14, SYTO 16, SYTO 21, SYTO RNA Select, SYTO 24, SYTO 25 and any equivalents thereof. The dye is used to "activate" WBCs and nRBCs, and "screen out" unlysed RBCs and fragments of RBCs based on a fluorescence trigger configured in the hematology analyzer. The dye is typically present at a concentration of from about 0.1 ng/mL to about 0.1 mg/mL. While various dyes are available, the dye selected is generally paired with the excitation source of the hematology analyzer such that a single exclusive dye is used to stain and excite fluorescence emission in nRBCs and all WBC sub-populations intended to be identified, quantified, and/or analyzed. As such, a single (i.e., exclusive) dye can be used to identify, quantify, and analyze nRBCs and all the WBC subpopulations at once.

In one embodiment, a fluorescent dye is provided in a reagent, with combinations of 1) at least one surfactant, 2) at least one buffer, 3) at least one salt, and/or 4) at least antimicrobial agent, in sufficient quantities for carrying out staining and activating up to $1,000 \times 10^3$ cells per microliter. The at least one surfactant, such as "TRITON" X-100 or saponin, is used to destroy the membranes of RBC, and reduce the sizes of fragments of RBCs. The at least one surfactant is typically present at a concentration of from about 0.001% to about 5%. The at least one antimicrobial agent, such as those from "TRIADINE" or "PROCLIN" families, is used to prevent the contamination of the reagent from microbes. The concentration of the at least one antimicrobial agent is sufficient to preserve the reagent for the shelf life required. The at least one buffer, such as phosphate buffered saline (PBS) or 4-(2-hydroxyethyl)-1-piperazineethanesulfonic acid (HEPES), is used to adjust the pH of reaction mixture for controlling lysis of RBCs and preserving WBCs. The at least one buffer is typically present at a concentration of from about 0.01% to about 3%. The pH typically ranges from about 3 to about 12. The at least one salt, such as NaCl or $Na_2SO_4$, is used to adjust the osmolality to increase the effect of lysing and/or optimize WBC preservation. The at least one salt may be present at a concentration of from about 0.01% to about 3%. In certain cases, the at least one buffer can serve as the at least one salt, or the at least one salt can serve as the at least one buffer. In general, lower osmolality, or hypotonicity, is used to accelerate the lysis of RBCs. The osmolality typically ranges from about 20 to about 250 mOsm.

Lysis of RBCs can be made to occur at a temperature above room temperature (e.g., between about 30° C. to about 50° C., such as about 40° C.) over a relatively short period of time (e.g., less than about 25 seconds, less than about 17 seconds, or even less than about 9 seconds), following mixing of the sample of blood and the reagent at a ratio of about one part by volume sample to about 35 parts by volume reagent. The data for analysis is collected with a plurality of optical channels and at least one fluorescence channel.

Figure 1A:
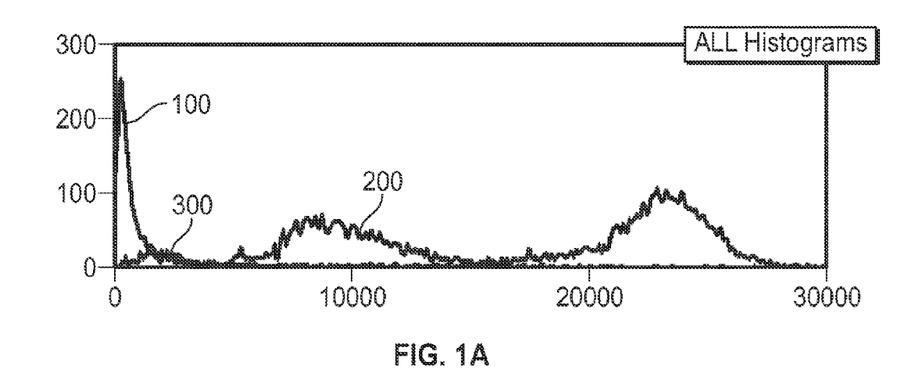
FIGS. 1A-1D show histograms of a sample of whole blood, showing WBCs, nRBCs, and residues of RBCs following lysis.
Figure 1B:
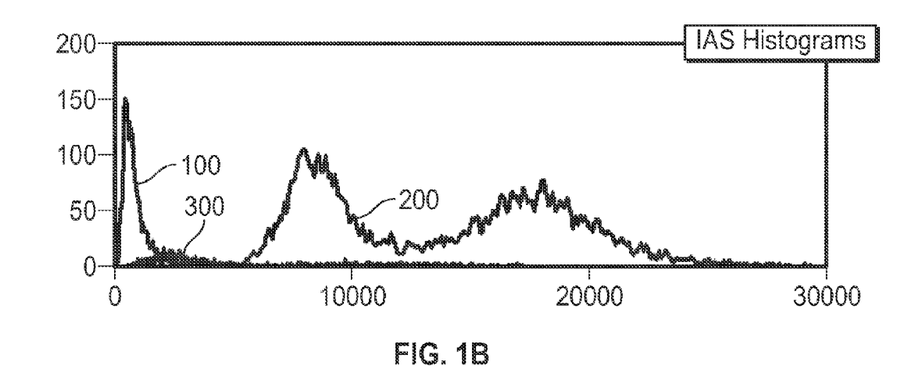
Figure 1C:
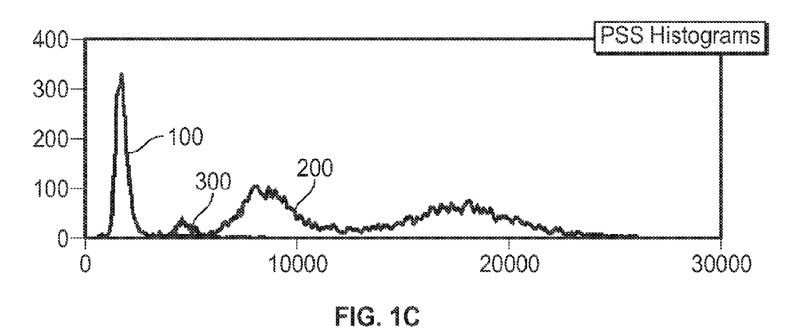
Figure 1D:
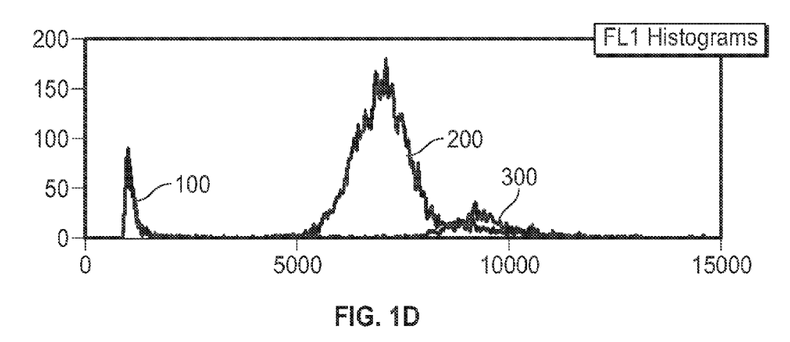

FIGS. 1A-1D show histograms of a sample of whole blood, showing the separation of WBCs, nRBCs, and residues of RBCs following lysis, based on optical and fluorescence measurements. More specifically, FIG. 1A is a histogram showing separation of particles based on measurements of axial light loss (ALL). FIG. 1B is a histogram showing separation of particles based on measurements of intermediate angle scatter (IAS). FIG. 1C is a histogram showing separation of particles based on measurements of 90° polarized side scatter (PSS). FIG. 1D is a histogram showing separation of particles based on measurements of fluorescence (FL1). In the histograms, the horizontal axis indicates the value of the detection channel (or the names of the channels, i.e., ALL, IAS, PSS, or FL1). The vertical axis indicates counts of components of the sample of blood. In the histograms, the lines 100 indicate residues of RBCs, lines 200 indicate WBCs, and lines 300 indicate nRBCs. As shown by comparing FIG. 1D to FIGS. 1A-1C, fluorescence information, rather than optical measurements, shows much better separation between the nuclei-containing particles (e.g., WBCs and nRBCs) and non-nuclei-containing particles (residues of RBCs). As used herein, "residues of RBCs" is synonymous with "fragments of RBCs."

(2) Use of a Fluorescence Trigger.

Blood cells emit different magnitudes of fluorescence signals upon excitation of the fluorescent dye by a source of light. The differences in magnitude of fluorescence signals arise from the quantity of nucleic acids, namely DNA, inside the cells. The greater the quantity of DNA, the greater the likelihood of higher fluorescence signals. Also, efficacy of penetration of cell membranes, size of the dye, binding kinetics between the dye and DNA, affinity between the dye and DNA, and other factors, affect the fluorescence signals. Mature RBCs emit minimal fluorescence signals because there is no DNA within mature RBCs. nRBCs emit very strong fluorescence signals, because not only is DNA inside nuclei of nRBCs, but also the staining is easier because membranes of nRBCs are destroyed during the lysis procedure. Unlysed RBCs or RBC fragments do not emit fluorescence, although they may emit very weak auto-fluorescence. As shown with reference to FIG. 1D, the cells that emit much stronger fluorescence signals are the cells having nuclei, namely, all WBCs and nRBCs (when present).

As such, the systems and methods presented herein use a fluorescence trigger for collecting and analyzing WBCs and nRBC. For example, a fluorescence trigger, usually set between signals from RBCs and signals from WBCs and nRBCs, can be used to collect signals from WBCs and nRBCs for subsequent analysis.

(3) Use of a Plurality of Optical Channels and at Least One Fluorescence Channel for Analysis.

As used herein, the expression "fluorescence information" means data collected from a fluorescence channel of a hematology analyzer. As used herein, the expression "fluorescence channel" means a detection device, such as a photomultiplier tube, set at an appropriate wavelength band for measuring the quantity of fluorescence emitted from a sample.

In one embodiment, the blood sample analysis is conducted by means of Multiple

Angle Polarized Scattering Separation technology (MAPSS), with enhancement from fluorescence information. At least one photodiode, or at least one photomultiplier tube, or both at least one photodiode and at least one photomultiplier tube, are needed to detect light scattered by each blood cell passing through a flow cell. Two or more photodiodes are used for measuring ALL signals, which measure about 0° scatter, and IAS signals, which measure low angle (e.g., about 3° to about 15°) scatter. Two or more photomultiplier tubes are used for detecting 90° polarized side scatter (PSS) signals and 90° depolarized side scatter (DSS) signals. Additional photomultiplier tubes are needed for FL1 measurements within appropriate wavelength range(s), depending on the choice of wavelength of the source of light. Each event captured on the system thus exhibits a plurality of dimensions of information, such as ALL, IAS (one or more channels), PSS, DSS, and fluorescence (one or more channels). The information from these detection channels is used for further analysis of blood cells.

Figure 2:
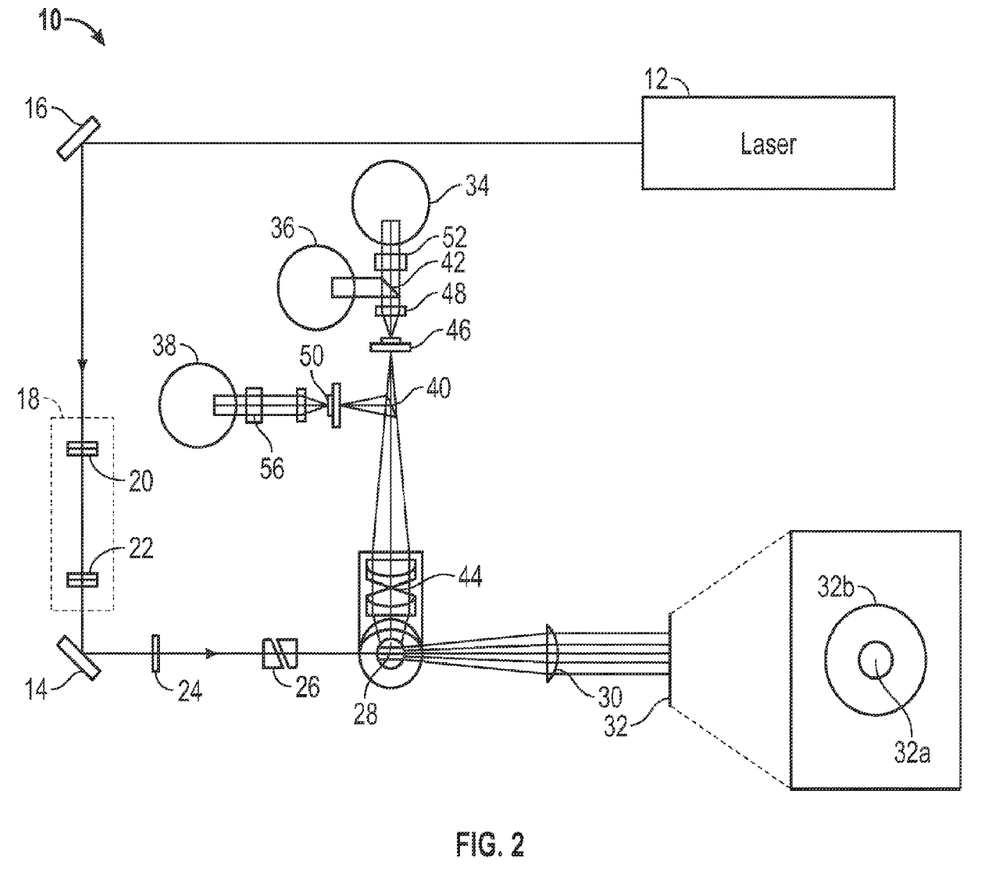
FIG. 2 is a schematic diagram illustrating a hematology instrument.

FIG. 2 is a schematic diagram illustrating the illumination and detection optics of an apparatus suitable for hematology analysis (including flow cytometry). Referring now to FIG. 2, an apparatus 10 comprises a source of light 12, a front minor 14 and a rear mirror 16 for beam bending, a beam expander module 18 containing a first cylindrical lens 20 and a second cylindrical lens 22, a focusing lens 24, a fine beam adjuster 26, a flow cell 28, a forward scatter lens 30, a bulls-eye detector 32, a first photomultiplier tube 34, a second photomultiplier tube 36, and a third photomultiplier tube 38. The bulls-eye detector 32 has an inner detector 32a for 0° light scatter and an outer detector 32b for 7° light scatter.

In the discussion that follows, the source of light is preferably a laser. However, other sources of light can be used, such as, for example, lamps (e.g., mercury, xenon). The source of light 12 can be a vertically polarized air-cooled Coherent Cube laser, commercially available from Coherent, Inc., Santa Clara, Calif. Lasers having wavelengths ranging from 350 nm to 700 nm can be used. Operating conditions for the laser are substantially similar to those of lasers currently used with "CELL-DYN" automated hematology analyzers.

Additional details relating to the flow cell, the lenses, the focusing lens, the fine-beam adjust mechanism and the laser focusing lens can be found in U.S. Pat. No. 5,631,165, incorporated herein by reference, particularly at column 41, line 32 through column 43, line 11. The forward optical path system shown in FIG. 2 includes a spherical plano-convex lens 30 and a two-element photo-diode detector 32 located in the back focal plane of the lens. In this configuration, each point within the two-element photodiode detector 32 maps to a specific collection angle of light from cells moving through the flow cell 28. The detector 32 can be a bulls-eye detector capable of detecting axial light loss (ALL) and intermediate angle forward scatter (IAS). U.S. Pat. No. 5,631,165 describes various alternatives to this detector at column 43, lines 12-52.

The first photomultiplier tube 34 (PMT1) measures depolarized side scatter (DSS).

The second photomultiplier tube 36 (PMT2) measures polarized side scatter (PSS), and the third photomultiplier tube 38 (PMT3) measures fluorescence emission from 440 nm to 680 nm, depending upon the fluorescent dye selected and the source of light employed. The photomultiplier tube collects fluorescent signals in a broad range of wavelengths in order to increase the strength of the signal. Side-scatter and fluorescent emissions are directed to these photomultiplier tubes by dichroic beam splitters 40 and 42, which transmit and reflect efficiently at the required wavelengths to enable efficient detection. U.S. Pat. No. 5,631,165 describes various additional details relating to the photomultiplier tubes at column 43, line 53 though column 44, line 4.

Sensitivity is enhanced at photomultiplier tubes 34, 36, and 38, when measuring fluorescence, by using an immersion collection system. The immersion collection system is one that optically couples the first lens 30 to the flow cell 28 by means of a refractive index matching layer, enabling collection of light over a wide angle. U.S. Pat. No. 5,631,165 describes various additional details of this optical system at column 44, lines 5-31.

The condenser 44 is an optical lens system with aberration correction sufficient for diffraction limited imaging used in high resolution microscopy. U.S. Pat. No. 5,631,165 describes various additional details of this optical system at column 44, lines 32-60.

The functions of other components shown in FIG. 2, i.e., a slit 46, a field lens 48, and a second slit 50, are described in U.S. Pat. No. 5,631,165, at column 44, line 63 through column 45, line 26. Optical filters 52 or 56 and a polarizer 52 or 56, which are inserted into the light paths of the photomultiplier tubes to change the wavelength or the polarization or both the wavelength and the polarization of the detected light, are also described in U.S. Pat. No. 5,631,165, at column 44, line 63 through column 45, line 26. Optical filters that are suitable for use herein include bandpass filters and long-pass filters.

The photomultiplier tubes 34, 36, and 38 detect either side-scatter (light scattered in a cone whose axis is approximately perpendicular to the incident laser beam) or fluorescence (light emitted from the cells at a different wavelength from that of the incident laser beam).

While select portions of U.S. Pat. No. 5,631,165 are referenced above, U.S. Pat. No. 5,631,165 is incorporated herein by reference in its entirety.

The optical and fluorescence information collected may then be used to distinguish (or differentiate) nRBCs from WBCs (and WBC sub-populations). For example, two-dimensional cytograms (e.g., cytograms showing PSS vs. ALL; ALL vs. IAS; and/or FL1 vs. ALL/IAS/PSS) can be used to identify and distinguish particles.

Figure 3A:
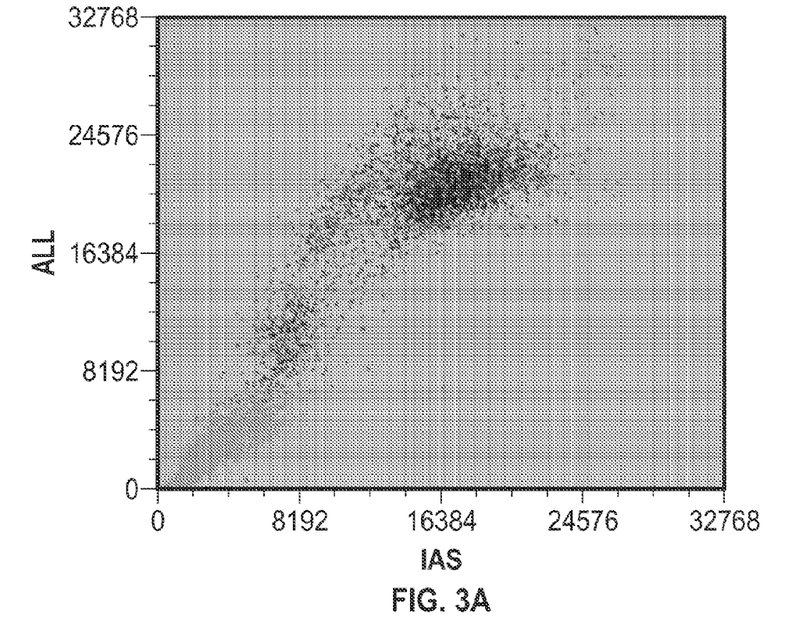
FIG. 3A is a cytogram depicting axial light loss vs. intermediate angle scatter.
Figure 3B:
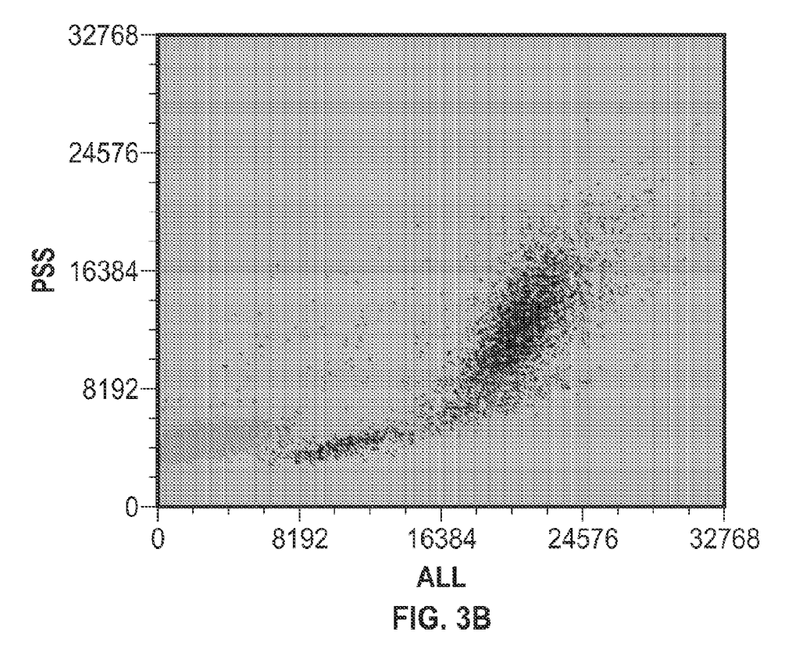
FIG. 3B is a cytogram depicting 90° polarized side scatter vs. axial light loss.
Figure 3C:
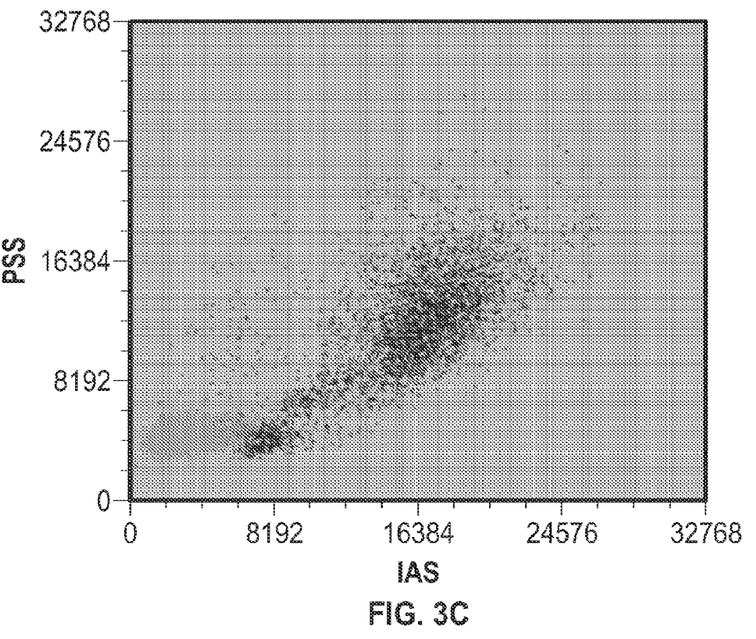
FIG. 3C is a cytogram depicting 90° polarized side scatter vs. intermediate angle scatter.
Figure 3D:
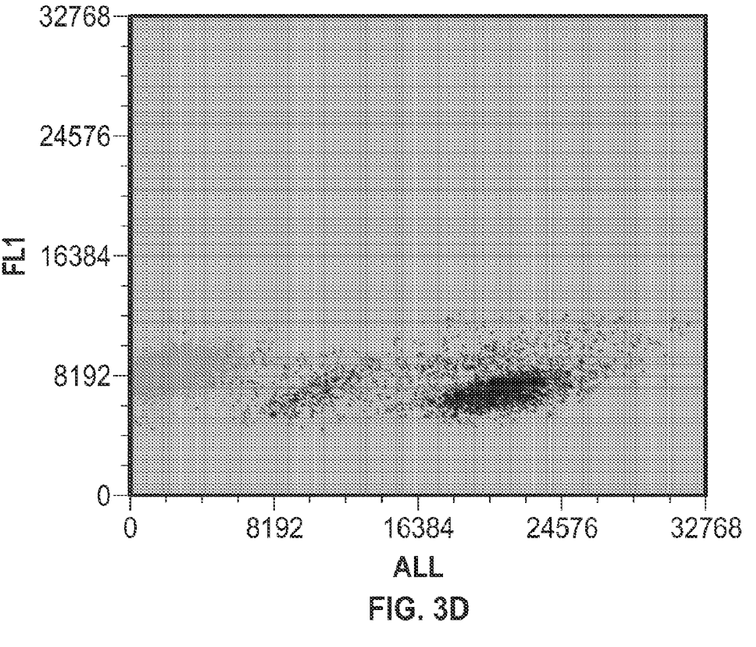
FIG. 3D is a cytogram depicting FL1 vs. axial light loss.
Figure 3E:
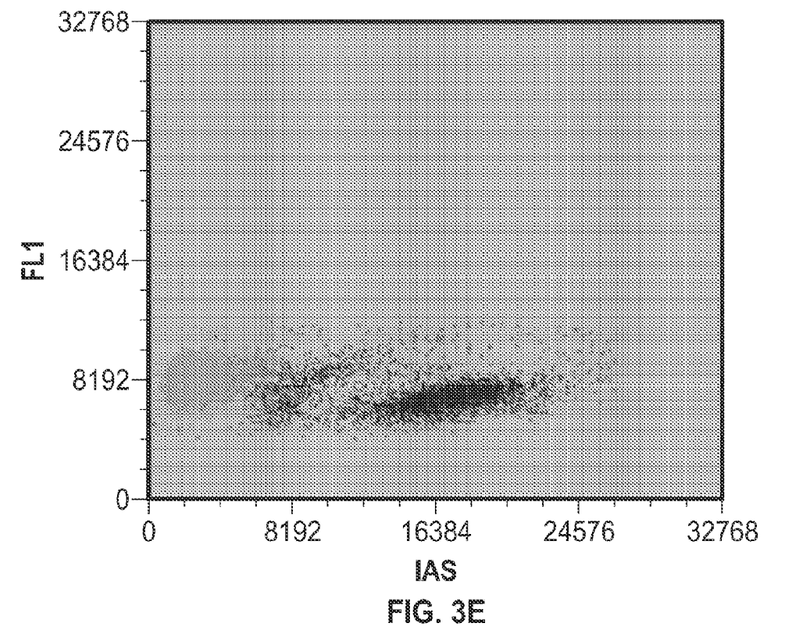
FIG. 3E is a cytogram depicting FL1 vs. intermediate angle scatter.
Figure 3F:
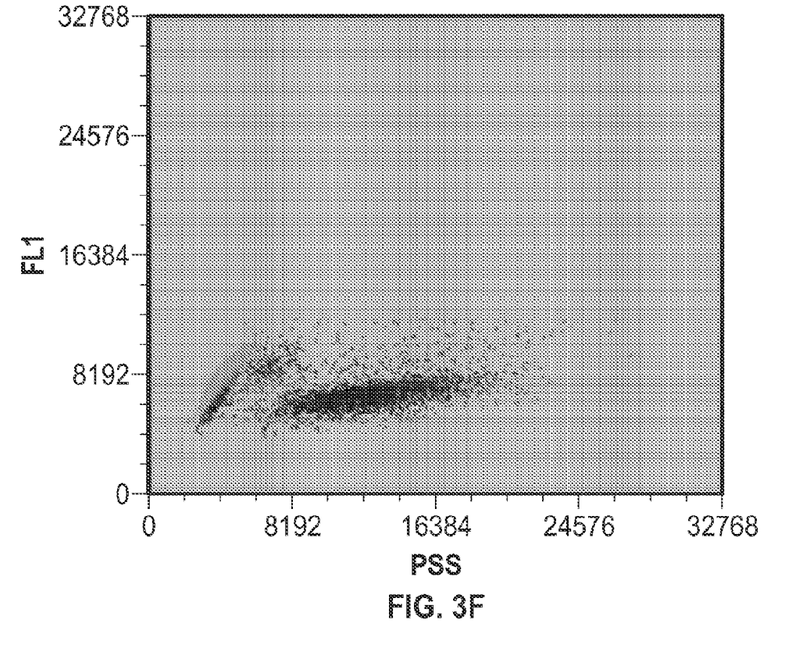
FIG. 3F is a cytogram depicting FL1 vs. 90° polarized side scatter.

FIGS. 3A-3F are cytograms illustrating an analysis of a sample of blood containing nRBCs at a % NRBC of 75%. More specifically, FIG. 3A is a cytogram depicting axial light loss vs. intermediate angle scatter. FIG. 3B is a cytogram depicting 90° polarized side scatter vs. axial light loss. FIG. 3C is a cytogram depicting 90° polarized side scatter vs. intermediate angle scatter. FIG. 3D is a cytogram depicting FL1 vs. axial light loss. FIG. 3E is a cytogram depicting FL1 vs. intermediate angle scatter. FIG. 3F is a cytogram depicting FL1 vs. 90° polarized side scatter. The % NRBC values obtained from the cytograms were 80.7 (as determined by manual gating using PSS v. ALL) and 76.3 (as determined by auto-clustering analysis carried out with MATLAB software).

Figure 4A:
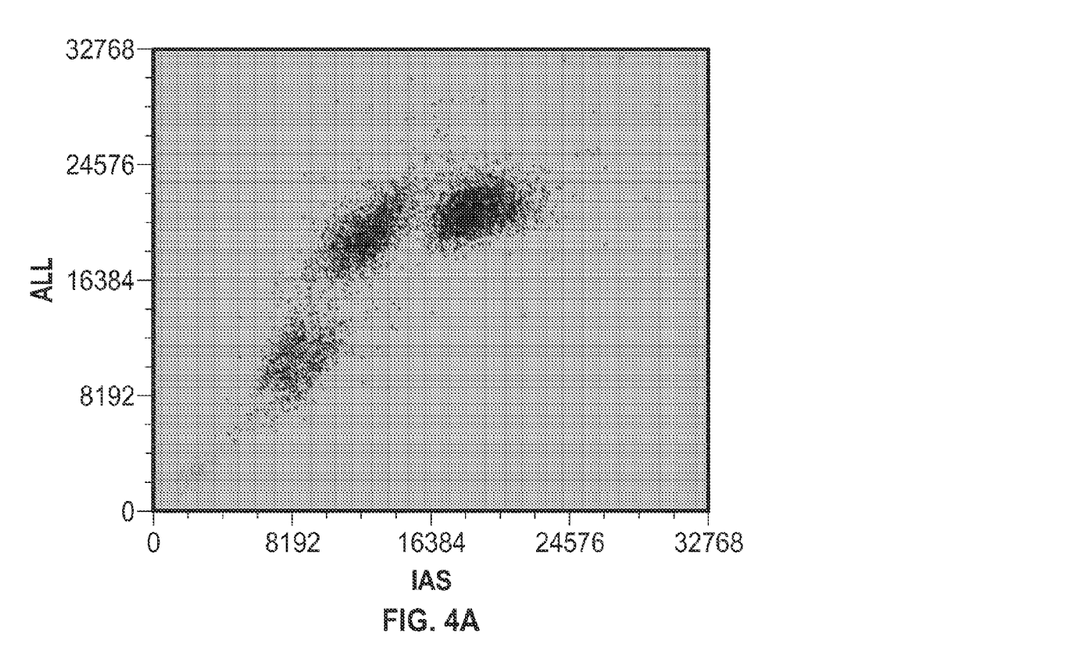
FIG. 4A is a cytogram depicting axial light loss vs. intermediate angle scatter.
Figure 4B:
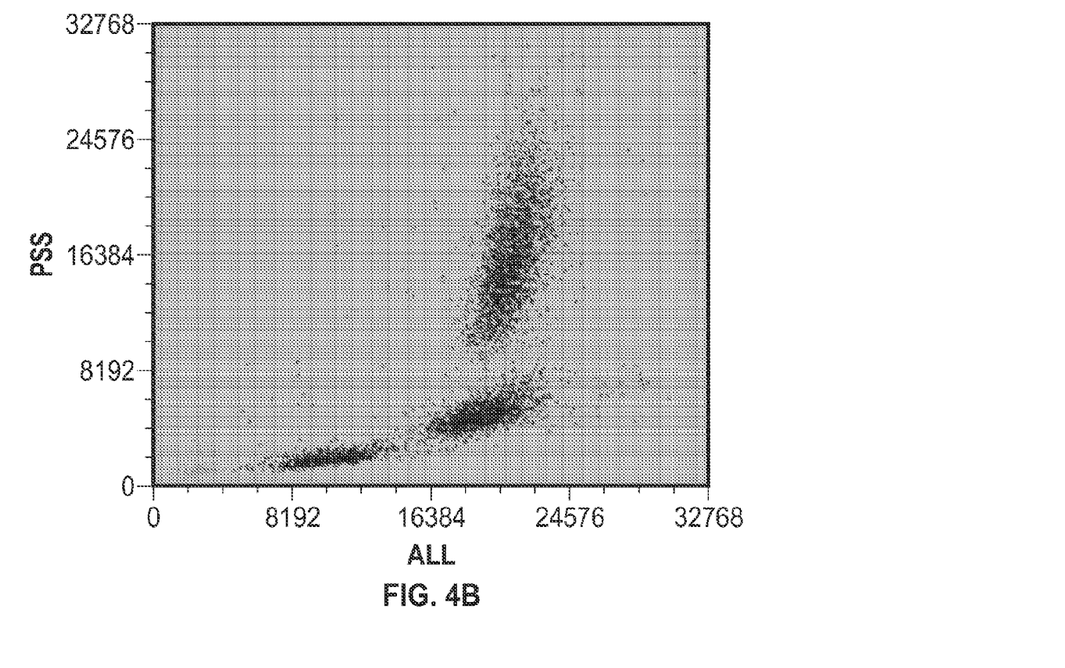
FIG. 4B is a cytogram depicting 90° polarized side scatter vs. axial light loss.
Figure 4C:
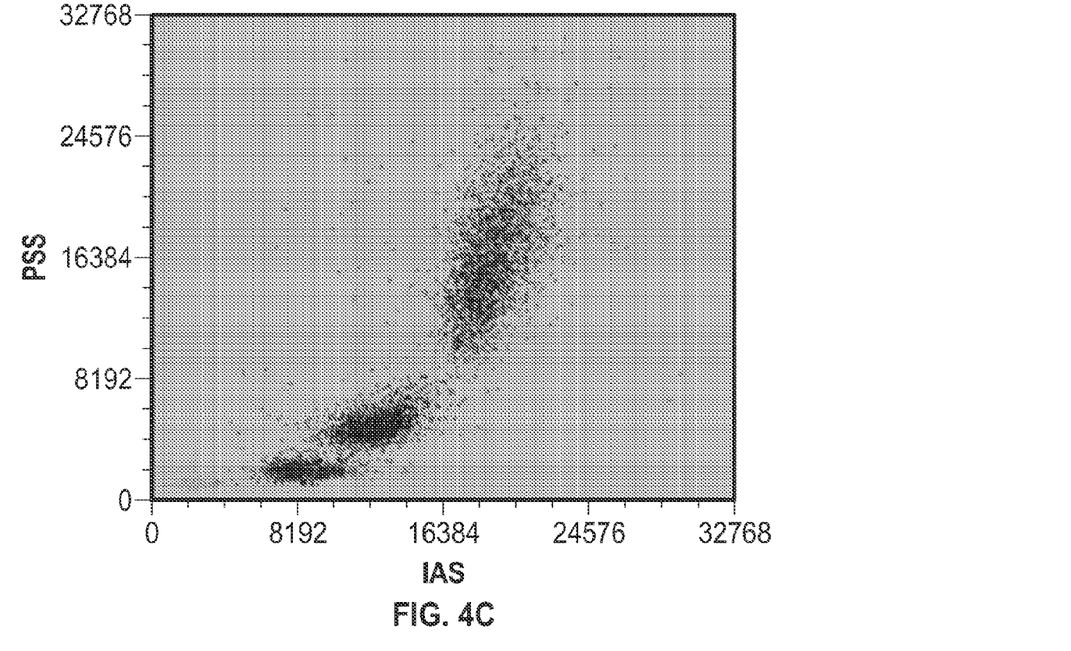
FIG. 4C is a cytogram depicting 90° polarized side scatter vs. intermediate angle scatter.
Figure 4D:
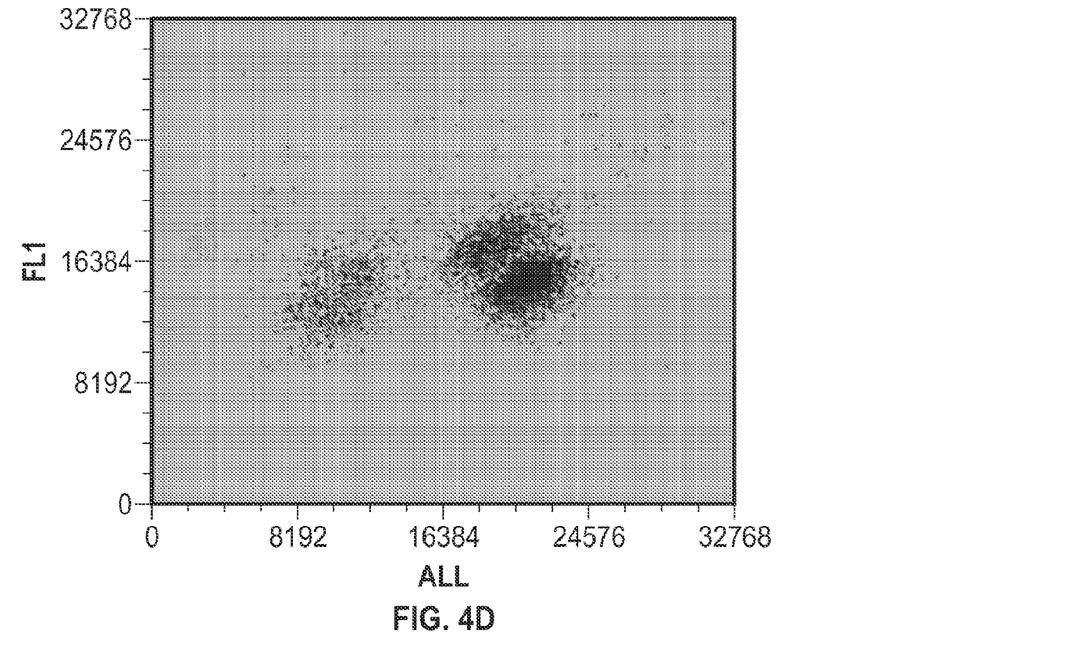
FIG. 4D is a cytogram depicting FL1 vs. axial light loss.
Figure 4E:
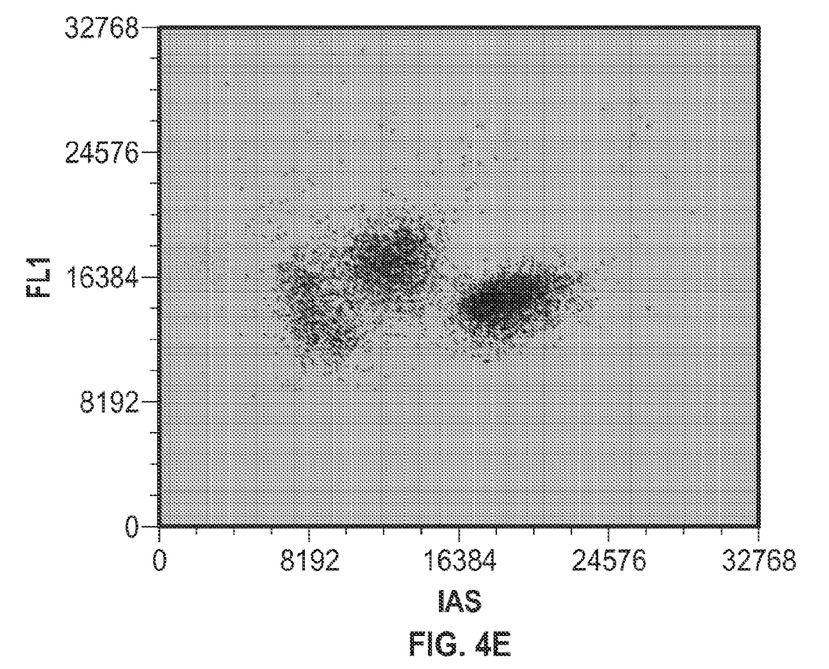
FIG. 4E is a cytogram depicting FL1 vs. intermediate angle scatter.
Figure 4F:
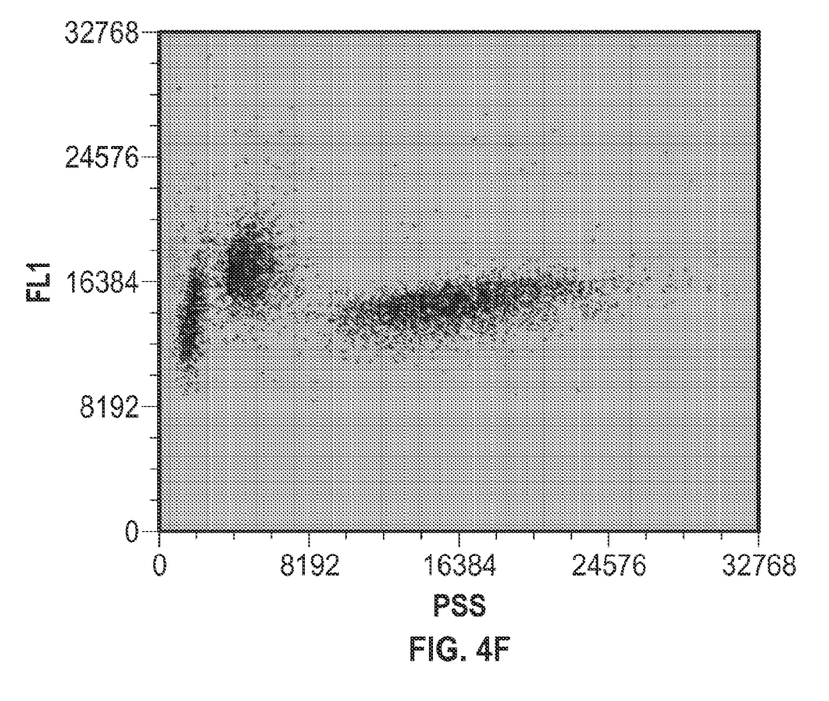
FIG. 4F is a cytogram depicting FL1 vs. 90° polarized side scatter.

FIGS. 4A-4F are cytograms illustrating an analysis of a sample of blood containing nRBCs as a % NRBC of 1.0%. More specifically, FIG. 4A is a cytogram depicting axial light loss vs. intermediate angle scatter. FIG. 4B is a cytogram depicting 90° polarized side scatter vs. axial light loss. FIG. 4C is a cytogram depicting 90° polarized side scatter vs. intermediate angle scatter. FIG. 4D is a cytogram depicting FL1 vs. axial light loss. FIG. 4E is a cytogram depicting FL1 vs. intermediate angle scatter. FIG. 4F is a cytogram depicting FL1 vs. 90° polarized side scatter. The % NRBC values obtained from the cytograms were 1.2 (as determined by manual gating using PSS v. ALL) and 1.2 (as determined by auto-clustering analysis carried out with MATLAB software).

In a study using a total of 136 samples containing nRBCs, both manual microscope reviews and "CELL-DYN" Sapphire™ hematology analyzer results were used as reference for quantifications of nRBCs. Acridine orange, at a concentration of 3 μg/mL, was included in the a reagent. The sample of blood and the reagent were mixed at a ratio of one part by volume sample to 35 parts by volume of reagent. The mixture was incubated for a period of 25 seconds at a temperature of 40° C. A sample measurement duration of 9 seconds was applied, with FL1 used as the sole trigger. Measurements of ALL, IAS, PSS, and FL1 were collected for each sample. The data was analyzed using both manual gating (PSS vs. ALL, or PSS vs. IAS) and auto-clustering analysis using MATLAB software. The correlations of % nRBC between the results from the method of the present invention, and reference results were reported as shown in FIGS. 5-8.

Figure 5:
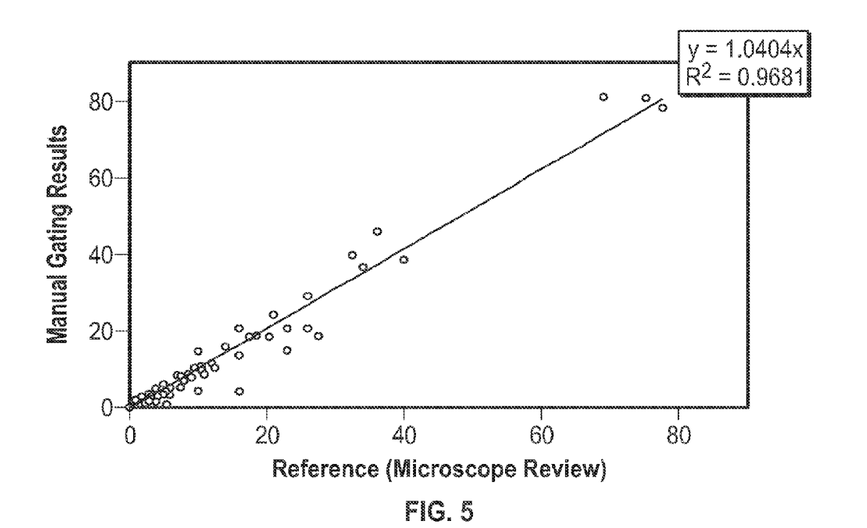
FIG. 5 is a plot illustrating correlation of % NRBC as determined by manual gating vs. reference results, wherein the reference results were obtained by a microscope review.

FIG. 5, for example, compares results (obtained by manual gating) against reference results, wherein the reference results were obtained by a microscope review. As shown, the systems and methods of the present invention produced results in accordance with the slope and $R^2$ formula of: $Y=1.0404X; (R^2=0.968)$.

Figure 6:
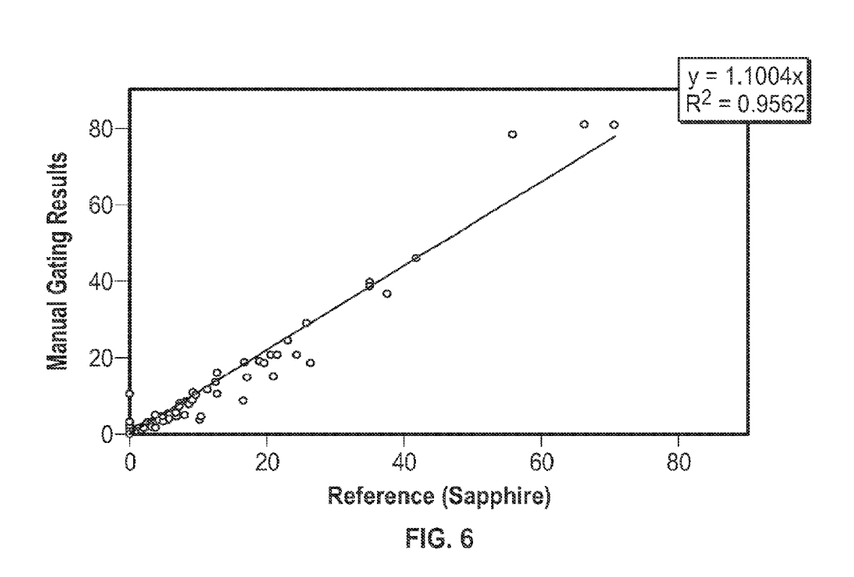
FIG. 6 is a plot illustrating correlation of % NRBC as determined by manual gating vs. reference results, wherein the reference results were obtained by a "CELL-DYN" Sapphire™ hematology analyzer.

FIG. 6 compares results (obtained by manual gating) against reference results, wherein the reference results were obtained by a "CELL-DYN" Sapphire™ hematology analyzer. As shown, the systems and methods of the present invention produced results in accordance with the slope and $R^2$ formula of: $Y=1.1004X; (R^2=0.956)$.

Figure 7:
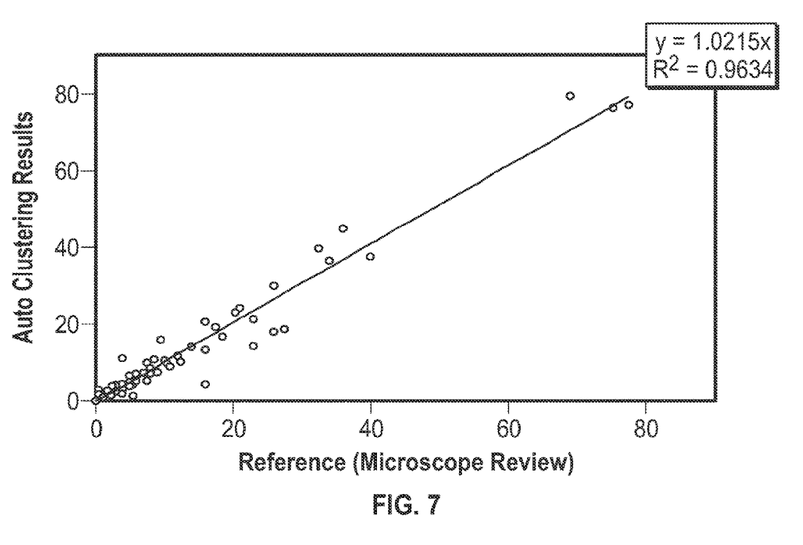
FIG. 7 is a plot illustrating correlation of % NRBC, as determined by auto-clustering vs. reference results, wherein the reference results were obtained by a microscope review.

FIG. 7 compares results (obtained by auto-clustering) against reference results, wherein the reference results were obtained by a microscope review. As shown, the systems and methods of the present invention produced results in accordance with the slope and $R^2$ formula of: $Y=1.0215X; (R^2=0.963)$.

Figure 8:
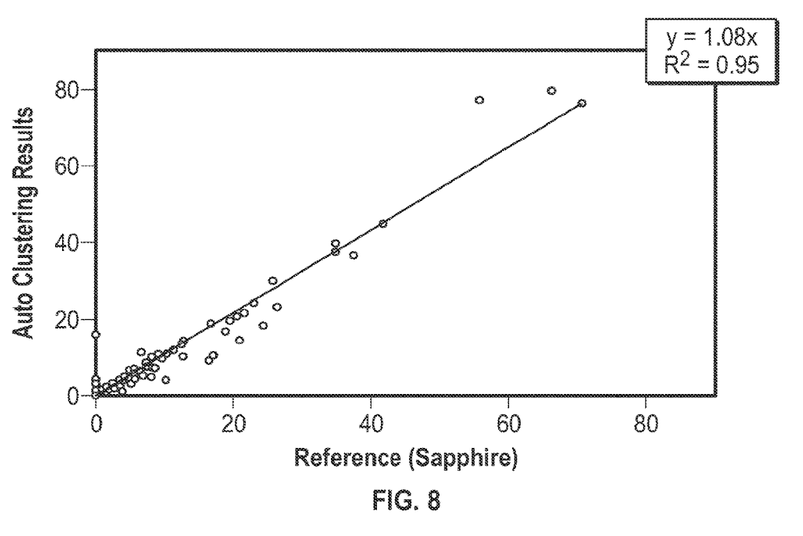
FIG. 8 is a plot illustrating correlation of % NRBC, as determined by auto-clustering vs. reference results, wherein the reference results were obtained by a "CELL-DYN" Sapphire™ hematology analyzer.

FIG. 8 compares results (obtained by auto-clustering) against reference results, wherein the reference results were obtained by a "CELL-DYN" Sapphire™ hematology analyzer. As shown, the systems and methods of the present invention produced results in accordance with the slope and $R^2$ formula of: $Y=1.0800X (R^2=0.950)$ Bhattacharyya distances (BD) between nRBCs and lymphocytes were also calculated based upon the mean positions of the clusters and distribution coefficients of variation. The cluster separation is considered to be "good" if BD exceeds 3 and is considered to be "acceptable" if BD is greater than 2 and less than or equal to 3. The average BD value for the tests were 4.64±1.89, ranging from 2.10 to 11.95, for the 136 samples. Good separations (in which BD exceeds 3) between nRBCs and lymphocytes were observed in more than 85% (116/136) of samples containing nRBCs.

In contrast to the difficulty of balancing "over-lysing" and "under-lysing" for traditional methods of measuring nRBCs, the methods described herein preserve WBCs and provide the best separation between nRBCs and lymphocytes (the WBC sub-population closest to nRBCs). Further, interference from fragments of RBCs is substantially eliminated.

Additional Embodiments

In another embodiment, there is provided a hematology analyzer for conducting a nucleated red blood cell (nRBC) analysis on a blood sample that has been dyed with a fluorescent dye, wherein the fluorescent dye is cell membrane permeable and nucleic acid binding. The analyzer comprises an excitation source positioned to excite particles within the blood sample. The analyzer also comprises a plurality of detectors including: (1) an axial light loss detector positioned to measure axial light loss from the excited blood sample, (2) an intermediate angle scatter detector positioned to measure intermediate angle scatter from the excited blood sample, (3) a side scatter detector positioned to measure 90° side scatter from the excited blood sample, and (4) a fluorescence detector positioned to measure fluorescence emitted from the excited blood sample. The analyzer also comprises a processor configured to: (a) receive the measurements of (1) axial light loss, (2) intermediate angle scatter, (3) 90° side scatter, and (4) fluorescence from the plurality of detectors, and (b) perform a nRBC differential analysis of the blood sample, based on all four measurements, for particles that emit fluorescence above a fluorescence threshold. The side scatter detector may be a polarized side scatter detector positioned to measure 90° polarized side scatter from the excited blood sample. The hematology analyzer may further comprise a depolarized side scatter detector positioned to measure 90° depolarized side scatter from the excited blood sample. The processor may be further configured to pre-screen the received measurements to remove from consideration any particles that do not meet the fluorescence threshold. The axial light loss detector can measure axial light loss at 0° scatter. The intermediate angle scatter detector can measure light angle scatter at about 3° to about 15°. The plurality of detectors can include one or more photomultiplier tubes. The excitation source may be a laser configured to emit light at a wavelength corresponding to the fluorescent dye. The fluorescent dye can be selected to correspond with the excitation source.

The hematology analyzer may further comprise an incubation subsystem for diluting the blood sample with a reagent. The reagent can include the fluorescent dye and a lysing agent. The reagent may alternatively comprise (a) at least one surfactant, (b) at least one buffer or at least one salt, (c) at least one antimicrobial agent, and (d) the fluorescent dye. The incubation subsystem may be configured to incubate the blood sample with the reagent for a period of time of less than about 25 seconds, less than about 17 seconds, and/or less than about 9 seconds. The incubation subsystem may be configured to incubate the blood sample with the reagent at a temperature ranging from about 30° C. to about 50° C., such as a temperature of about 40° C.

In another embodiment, there is provided a method of performing a nucleated red blood cell nRBC analysis with an automated hematology analyzer. The method comprises the steps of: (a) diluting a sample of whole blood with a reagent, wherein the reagent includes a red blood cells (RBC) lysing agent and a cell membrane permeable, nucleic acid binding fluorescent dye; (b) incubating the diluted blood sample of step (a) for an incubation period of less than about 25 seconds, at a temperature ranging from about 30° C. to about 50° C.; (c) delivering the incubated sample from step (b) to a flow cell in the hematology analyzer; (d) exciting the incubated sample from step (c) with an excitation source as the incubated sample traverses the flow cell; (e) collecting a plurality of light scatter signals and a fluorescence emission signal from the excited sample; and (f) performing a nRBC analysis based on all the signals collected in step (e), while removing from consideration any particles within the diluted blood sample that do not meet a fluorescence threshold based on the fluorescence emission signal.

The reagent may include: (a) at least one surfactant, (b) at least one buffer or at least one salt, (c) at least one antimicrobial agent, and (d) at least one fluorescent dye. The excitation source may have a wavelength of from about 350 nm to about 700 nm. The fluorescence emission may be collected at a wavelength of from about 360 nm to about 750 nm, by a band-pass filter or a long-pass filter. The plurality of light scatter signals may include: (1) axial light loss, (2) intermediate angle scatter, and (3) 90° side scatter. The plurality of light scatter signals may include: (1) axial light loss, (2) intermediate angle scatter, (3) 90° polarized side scatter, and (4) 90° depolarized side scatter.

In yet another embodiment, there are provided systems and methods for counting nRBCs by means of an automated hematology analyzer. The systems and method include means for and the steps of: (a) diluting a whole blood sample containing nucleated red blood cells with at least one white blood cell reagent; (b) incubating the diluted sample of step (a) for a sufficient period of time within a selected temperature range to lyse red blood cells, allow nuclei of nucleated red blood cells to be exposed to the at least one white blood cell reagent, and allow at least one fluorescent dye to stain nuclei of nucleated red blood cells, and preserve white blood cells; (c) delivering the incubated sample of step (b) to a flow cell as a stream; (d) exciting the incubated sample with a source of light as the incubated sample traverses the flow cell; (e) collecting a plurality of optical scatter signals and at least one fluorescence emission signal simultaneously; and (f) differentiating and quantifying nucleated red blood cells by means of the optical information and fluorescence information collected in step (e). The systems and methods further include: (1) the use of at least one fluorescent dye to bind and stain nucleic acids in WBCs and the nuclei of nRBCs in a given sample of blood during the procedure for lysing RBCs, and to induce fluorescence emissions upon being excited by photons from a given source of light, such as a laser beam at an appropriate wavelength; (2) the use of a fluorescent trigger to separate and collect events that emit strong fluorescence (i.e., WBCs and nRBCs); and (3) the use of a plurality of optical channels and at least one fluorescent channel for collecting and analyzing data in order to identify nRBCs, and to separate nRBCs from WBCs. The systems and method described herein allows simultaneous analysis of WBCs and nRBCs. No additional reagent, preparation of samples, or analytical procedure is needed. Therefore, the method is efficient, cost-effective, and practical for modern diagnostic use.

In one embodiment, the invention is directed towards one or more computer systems capable of carrying out the functionality described herein. For example, any of the method/analysis steps discussed herein may be implemented in a computer system having one or more processors, a data communication infrastructure (e.g., a communications bus, cross-over bar, or network), a display interface, and/or a storage or memory unit. The storage or memory unit may include computer-readable storage medium with instructions (e.g., control logic or software) that, when executed, cause the processor(s) to perform one or more of the functions described herein. The terms "computer-readable storage medium," "computer program medium," and "computer usable medium" are used to generally refer to media such as a removable storage drive, removable storage units, data transmitted via a communications interface, and/or a hard disk installed in a hard disk drive. Such computer program products provide computer software, instructions, and/or data to a computer system, which also serve to transform the computer system from a general purpose computer into a special purpose computer programmed to perform the particular functions described herein. Where appropriate, the processor, associated components, and equivalent systems and sub-systems thus serve as examples of "means for" performing select operations and functions. Such "means for" performing select operations and functions also serve to transform a general purpose computer into a special purpose computer programmed to perform said select operations and functions.

Conclusion

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

The above Detailed Description refers to the accompanying drawings that illustrate one or more exemplary embodiments. Other embodiments are possible. Modifications may be made to the embodiment described without departing from the spirit and scope of the present invention. Therefore, the Detailed Description is not meant to be limiting. Further, the Summary and Abstract sections may set forth one or more, but not all exemplary embodiments of the present invention as contemplated by the inventor(s), and thus, are not intended to limit the present invention and the appended claims in any way.

What is claimed is:

1. A hematology analyzer for conducting a nucleated red blood cell (nRBC) analysis on a blood sample that contains a plurality of nRBCs, the analyzer comprising:
    an excitation source positioned to excite particles within the blood sample;
    a plurality of detectors including (1) an axial light loss detector positioned to measure axial light loss from the excited blood sample, (2) an intermediate angle scatter detector positioned to measure intermediate angle scatter from the excited blood sample, (3) a side scatter detector positioned to measure 90° side scatter from the excited blood sample, and (4) a fluorescence detector positioned to measure fluorescence emitted from the excited blood sample;
    a processor; and
    a non-transitory computer-readable memory medium comprising instructions that when executed cause the processor to:
        (a) dilute the blood sample with a reagent that includes a red blood cell (RBC) lysing agent and a cell membrane permeable, nucleic acid binding fluorescent dye;
        (b) incubate the diluted blood sample of step (a) for an incubation period of time;
        (c) deliver the incubated sample from step (b) to a flow cell in the hematology analyzer;
        (d) excite the incubated sample from step (c) with an excitation source as the incubated sample traverses the flow cell;
        (e) collect a plurality of light scatter signals and fluorescence emission signals from the excited sample;
        (f) prior to performing an nRBC differential analysis, exclude nuclei-free events and retain nuclei-containing events using only a fluorescence trigger that is limited to fluorescence emission signals and is set to a fluorescence magnitude that is greater than fluorescence emission signals from RBCs, including RBC fragments, and is less than fluorescence emission signals from white blood cells (WBCs) and nRBCs; and
        (g) perform the nRBC differential analysis on the nuclei-containing events collected in step (f).

2. The hematology analyzer of claim 1, wherein the side scatter detector is a polarized side scatter detector positioned to measure 90° polarized side scatter from the excited blood sample.

3. The hematology analyzer of claim 2, further comprising:
    a depolarized side scatter detector positioned to measure 90° depolarized side scatter from the excited blood sample.

4. The hematology analyzer of claim 1, wherein the axial light loss detector measures axial light loss at 0° scatter.

5. The hematology analyzer of claim 1, wherein the intermediate angle scatter detector measures light angle scatter at about 3° to about 15°.

6. The hematology analyzer of claim 1, wherein the plurality of detectors include one or more photomultiplier tubes.

7. The hematology analyzer of claim 1, wherein the excitation source is a laser.

8. The hematology analyzer of claim 7, wherein the laser is configured to emit light at a wavelength corresponding to the fluorescent dye.

9. The hematology analyzer of claim 1, wherein the fluorescent dye is selected to correspond with the excitation source.

10. The hematology analyzer of claim 1, further comprising:
    an incubation subsystem for diluting the blood sample with a reagent.

11. The hematology analyzer of claim 10, wherein the reagent includes the fluorescent dye and a lysing agent.

12. The hematology analyzer of claim 10, wherein the reagent includes (a) at least one surfactant, (b) at least one buffer or at least one salt, (c) at least one antimicrobial agent, and (d) the fluorescent dye.

13. The hematology analyzer of claim 10, wherein the incubation subsystem is configured to incubate the blood sample with the reagent for a period of time of less than 25 seconds.

14. The hematology analyzer of claim 10, wherein the incubation subsystem is configured to incubate the blood sample with the reagent for a period of time of less than 17 seconds.

15. The hematology analyzer of claim 10, wherein the incubation subsystem is configured to incubate the blood sample with the reagent for a period of time of less than 9 seconds.

16. The hematology analyzer of claim 10, wherein the incubation subsystem is configured to incubate the blood sample with the reagent at a temperature ranging from 30° C. to 50° C.

17. The hematology analyzer of claim 10, wherein the incubation subsystem is configured to incubate the blood sample with the reagent at a temperature of 40° C.

\* \* \* \* \*